US00PP32318P3

(12) United States Plant Patent
Hand et al.

(10) Patent No.: US PP32,318 P3
(45) Date of Patent: Oct. 13, 2020

(54) ***CANNABIS* PLANT NAMED 'MR2017002'**

(50) Latin Name: *Cannabis sativa*
Varietal Denomination: MR2017002

(71) Applicant: MedReleaf Corp., Toronto, Ontario (CA)

(72) Inventors: Andrew Hand, Bradford (CA); Alan Graziano, Toronto (CA)

(73) Assignee: Aurora Cannabis Enterprises Inc., Edmonton (CA)

( * ) Notice: Subject to any disclaimer, the term of this patent is extended or adjusted under 35 U.S.C. 154(b) by 0 days.

(21) Appl. No.: 16/501,409

(22) Filed: Apr. 9, 2019

(65) Prior Publication Data

US 2019/0313563 P1 Oct. 10, 2019

(30) Foreign Application Priority Data

Apr. 10, 2018 (CA) ..... PBR 18-9418

(51) Int. Cl.
*A01H 5/02* (2018.01)
*A01H 6/28* (2018.01)
*A61K 36/185* (2006.01)

(52) U.S. Cl.
USPC ..... Plt./258
CPC ..... *A01H 6/28* (2018.05); *A61K 36/185* (2013.01)

(58) Field of Classification Search
USPC ..... Plt./258, 263.1
CPC ... A01H 5/12; A01H 5/02; A01H 5/00; A01H 6/28; A61K 36/185; G06F 3/0481
See application file for complete search history.

*Primary Examiner* — June Hwu
(74) *Attorney, Agent, or Firm* — Christensen O'Connor Johnson Kindness PLLC

(57) ABSTRACT

A new cultivar of *Cannabis* named 'MR2017002' that is characterized by 13% THC and 0.1% CBD by dry weight, significant resistance to microbial growth, and a low number of intra-flower leaves on average for *Cannabis*.

2 Drawing Sheets

Genus and species: *Cannabis sativa.*
Variety denomination: 'MR2017002'.

CROSS REFERENCE TO RELATED APPLICATIONS

This application claims the benefit of priority under 35 U.S.C. 119 (f) to the application for Canadian Plant Breeders' Rights which was filed for the instant plant variety on Apr. 10, 2018, Application Number 18-9418.

BACKGROUND OF THE NEW PLANT

The present invention relates to a new and distinct variety of *Cannabis* grown for use as medical marijuana. The new cultivar is known botanically as *Cannabis sativa* and will be referred to hereinafter by the cultivar name 'MR2017002'.

'MR2017002' originated from a controlled cross in Markham, Ontario, Canada, between the female *Cannabis sativa* variety 'California Orange' and the male *Cannabis sativa* variety 'Skunk #1'.

Seeds from the cross were sown in Markham, Ontario, Canada and plants were screened for a number of traits including tetrahydrocannabinol (THC) and cannabidiol (CBD) levels, yield, flowering time, disease resistance and flower morphology. In July 2015, a single plant was selected having about 13% THC and 0.1% CBD by dry weight, significant resistance to microbial growth, and a low number of intra-flower leaves. The selection was named 'MR2017002'.

In July 2015, 'MR2017002' was first asexually propagated by apical stem cuttings approximately 10 cm long and having multiple auxiliary meristems, in Markham, Ontario, Canada. 'MR2017002' was found to reproduce true to type in successive generations of asexual propagation via vegetative cuttings in Markham, Ontario, Canada.

SUMMARY

The following traits have been repeatedly observed and represent the distinguishing characteristics of 'MR2017002'. 'MR2017002' has not been tested under all possible conditions and phenotypic differences may be observed with variations in environmental, climatic, and cultural conditions, without however, any variance in genotype.

1. 'MR2017002' exhibits approximately 13% THC by dry weight.
2. 'MR2017002' exhibits approximately 0.1% CBD by dry weight.
3. 'MR2017002' exhibits resistance to microbial growth.
4. 'MR2017002' exhibits lower number of intra-flower leaves compared to reference plant Girl Scout Cookies and/or low on average for *Cannabis*.

BRIEF DESCRIPTION OF THE PHOTOGRAPHS

The accompanying color photographs illustrate the overall appearance of 'MR2017002'. The photographs are of plants aged 8 to 9 weeks post-floral transition and grown in flower rooms under standard cultivation methods in Markham, Ontario, Canada, in February, 2018. The colors shown are as true as can be reasonably obtained by conventional photographic procedures.

Figure 1:
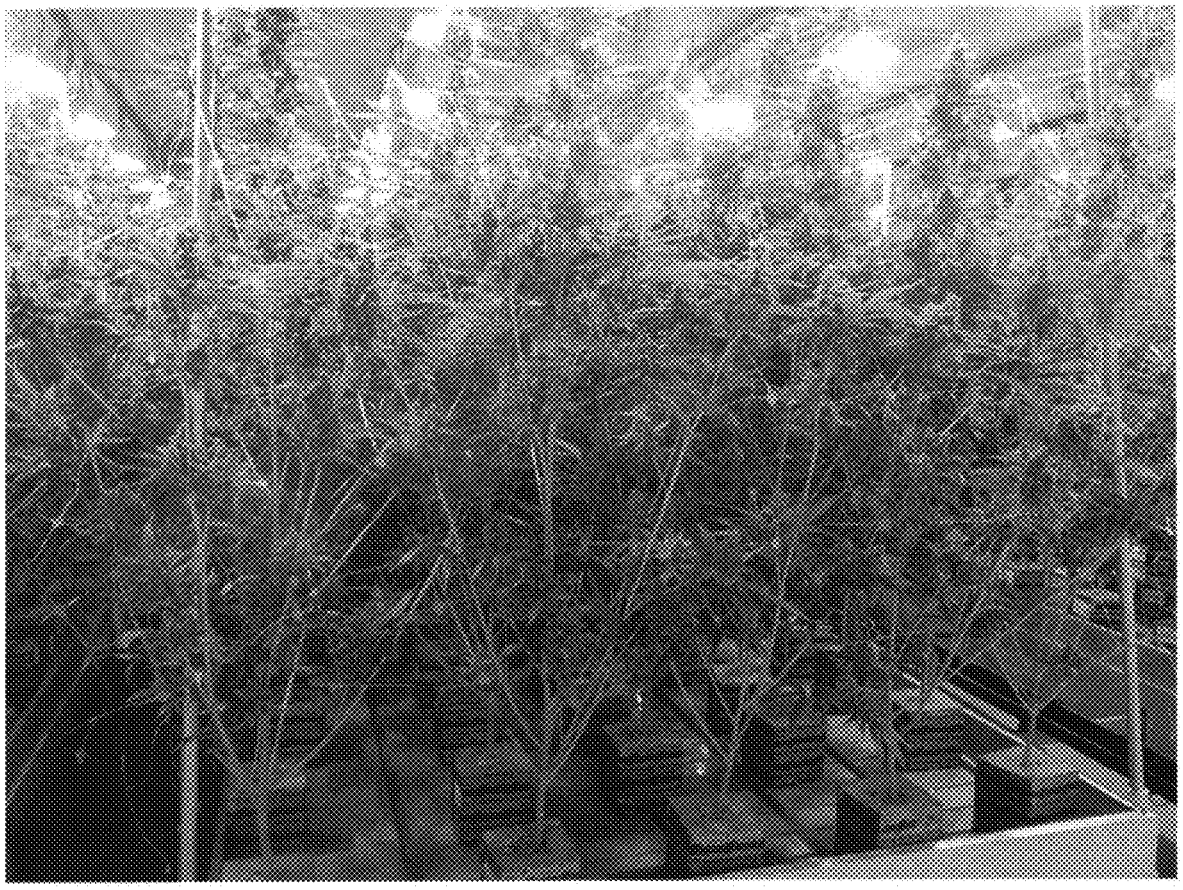

FIG. 1 depicts multiple, whole plant clones of 'MR2017002'.

Figure 2:
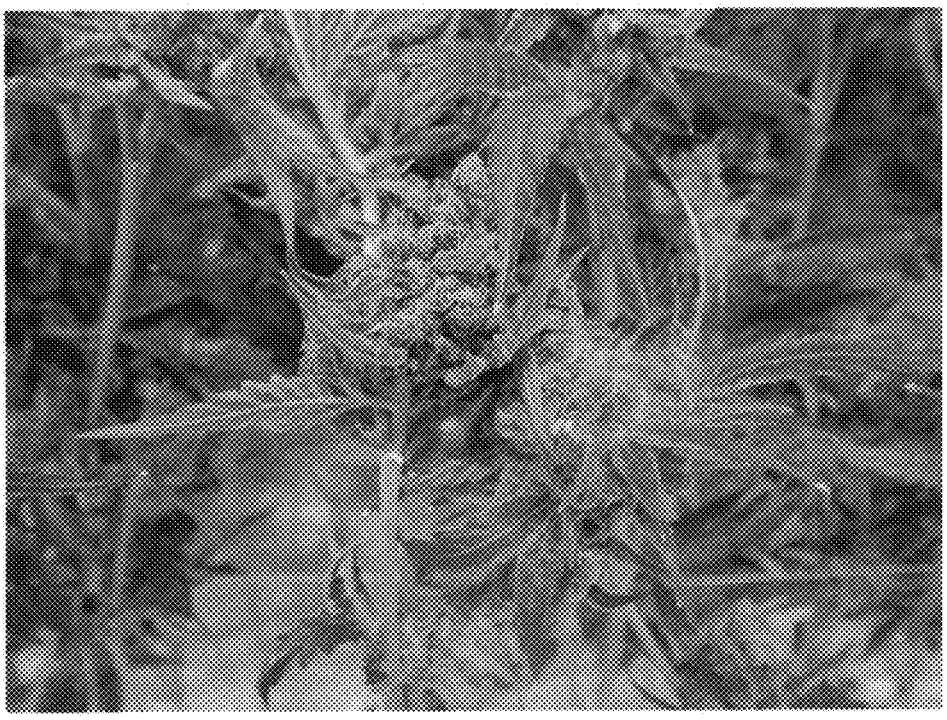

FIG. 2 presents a close-up view of a single inflorescence and foliage of 'MR2017002'.

BOTANICAL DESCRIPTION OF THE PLANT

The following is a detailed botanical description of the new *Cannabis* variety named 'MR2017002'. Data was collected in Markham, Ontario, Canada in 2015 and 2016 from plants 8 to 9 weeks post-floral transition.

Plants were flowered under standard indoor environmental conditions with High Pressure Sodium lamps. Clones were cut from healthy mothers and allowed to root for 14 to 18 days prior to being introduced to the flower room. The room was maintained at 18 hour days/6 hour nights for a week to allow the cuttings to establish adequate vegetative tissue. The floral transition was initiated by switching to 12 hour days and 12 hour nights. Flowering lasted 9 weeks before harvest, at which point morphological measurements were taken, samples were taken for chemical analysis, and yield was quantified. Hermaphroditic male flowers, if they show up, will do so around week 2-4. It's not all at once, they emerge over time.

Standard in-house developed nutrients were used throughout growth, and the plants were defoliated and pruned as necessary throughout the cycle.

Color determinations were made in accordance with the 2017 Munsell Plant Tissue Color Book, except where general color terms of ordinary dictionary significance are used.

Classification:
- *Family*.—Cannabaceae.
- *Genus*.—*Cannabis*.
- *Species*.—*Cannabis sativa*.
- *Common name*.—Marijuana.

Parentage:
- *Female parent*.—'California Orange'.
- *Male parent*.—'Skunk #1'.

Propagation:
- *Type*.—Clonal propagation from vegetative cuttings.
- *Time to produce a rooted young plant*.—18 days.
- *Root description*.—Fine and well-branched.
- *Rooting habit*.—Fine and well-branched.

Plant:
- *Use*.—Medical marijuana.
- *Plant height*.—80 cm to 110 cm.
- *Plant diameter*.—45 cm to 50 cm.
- *Proportion of female plants*.—High.
- *Proportion of male plants*.—N/A.
- *Proportion of hermaphrodite plants*.—Very low; hermaphroditic male flowers, if present, emerge over time around weeks 2-4.
- *Shipping quality*.—High.
- *Storage life*.—Long.

Stems:
- *Length*.—80 cm to 100 cm, same as overall plant height.
- *Width*.—8 mm to 10 mm.
- *Depth of main stem grooves*.—Shallow.
- *Color*.—2.5 GY 5/6.
- *Texture*.—Fibrous and Pubescent.
- *Lateral branch length*.—25 cm to 30 cm for shorter branches, 55 cm to 65 cm for longer branches.
- *Average number of nodes*.—29.
- *Average internode length*.—9 cm.

Leaves:
- *Type/form*.—Palmately compound.
- *Arrangement*.—Alternate.
- *Attachment*.—Petiolate.
- *Leaf width*.—14 cm to 16 cm for fully mature leaves.
- *Leaf length*.—12 cm to 13 cm for fully mature leaves.
- *Number of leaflets per leaf*.—5 to 7.
- *Leaflet shape*.—Lanceolate.
- *Leaflet length*.—3 cm to 6 cm for shorter leaflets, 12 cm to 14 cm for longer leaflets.
- *Leaflet width*.—0.7 cm to 0.8 cm for shorter leaflets, 1.5 cm to 2.5 cm for longer leaflets.
- *Leaflet margin*.—Serrate.
- *Leaflet apex*.—Acuminate.
- *Leaflet base*.—Attenuate.
- *Leaflet color, upper surface*.—7.5 GY 3/4.
- *Leaflet color, lower surface*.—7.5 GY 5/4.
- *Venation pattern, upper and lower leaflet surfaces*.—Pinnate.
- *Texture (both surfaces)*.—Pubescent, primarily on the abaxial side and along leaf vasculature.
- *Fragrance*.—Present, citrus and skunk.
- *Stipules*.—Present, 2 per node on either side of a petiole, attenuate.

Petioles:
- *Length*.—4 cm to 5.5 cm.
- *Diameter*.—0.3 cm.
- *Texture*.—Pubescent.
- *Color*.—A mix of 2.5 GY 5/6 and 5 RP 3/4.
- *Intensity of petiole anthocyanin*.—Very strong.

Inflorescence:
- *Blooming habit*.—Short day photoperiod sensitive.
- *Blooming period*.—50 days.
- *Attachment*.—Very short pedicel that clusters of calyces emanate from.
- *Fragrance*.—Citrus and skunk.
- *Inflorescence color*.—5 RP 3/4.
- *Number of inflorescences per plant*.—45 to 70.
- *Diameter (cm)*.—3 cm to 4 cm.
- *Length (cm)*.—3 cm to 4 cm.
- *Inflorescence anthocyanin*.—Strong presence of Anthocyanin A mix of 7.5 GY 6/10 and 5 RP 3/4.
- *Inflorescence THC content*.—Average of 13.41% by dry weight.

Reproductive organs:
- *Pistils*.—1.
- *Quantity (of stigmas) per flower*.—2.
- *Stigma length*.—Small, about 3-5 mm.
- *Stigma color*.—5Y 8/2 before senescence, 7.5 YR 6/6 post senescence.
- *Trichomes*.—Capitate-sessile, capitate-stalked, bulbous, and non-glandular (cystolith hairs); trichomes are present on almost all aerial organs but are present at highest concentration on female flowers (calyxes, bracts, etc.) as well as subtending intra-flower leaves.
- *Trichome color*.—Clear, may turn cloudy or amber during senescence.
- *Bracht size*.—Small, under 1 cm.
- *Bracht color*.—5 RP 3/4.
- *Pollen*.—Absent.

Disease and insect/pest resistance: 'MR2017002' exhibits resistance to aerobic bacteria, yeast and mold, and coliform bacteria as shown below in Table 1.

TABLE 1

| 'MR2017002'Disease resistance | |
|---|---|
| Average Aerobic Bacteria Count per plant, in colony forming units (CFUs) | 653 |
| Average Yeast and Mold Count per plant, in CFUs | 600 |
| Average coliform bacteria count per plant, in CFUs | 217 |

COMPARISON WITH PARENTAL LINES AND KNOWN VARIETY

'MR2017002' may be compared with its parental lines as follows. Whereas 'MR2017002' exhibits 13% THC by dry weight, the female parent exhibits 15% THC by dry weight and the male parent exhibits 8% THC by dry weight. Total THC and Total CBD were quantified with a Waters LC-MS/MS, running an Acetonitrile:Methanol:2 propanol gradient mobile phase containing formic acid through a Raptor ACR-18, 2.7 um, 2.1×150 mm column.

The closest variety of *Cannabis* known to the inventors is the variety 'Girl Scout Cookies'. 'MR2017002' can be distinguished from 'Girl Scout Cookies' by its increased resistance to microbial growth, as shown in Table 2 below. Variety 'MR2017002' can also be distinguished from the variety 'Girl Scout Cookies' on the basis that it does not contain many intra-flower leaves as 'Girl Scout Cookies'.

TABLE 2

| Comparison with commercial variety 'Girl Scout Cookies' | | |
|---|---|---|
| | 'MR2017002' | 'Girl Scout Cookies' |
| Average Aerobic Bacteria Count per plant, in CFUs | 653 | 59270 |
| Average Yeast and Mold Count per plant, in CFUs | 600 | 52450 |
| Average coliform bacteria count per plant, in CFUs | 217 | 760 |

We claim:

1. A new and distinct cultivar of *Cannabis* plant named 'MR2017002' as described and illustrated herein.

* * * * *